United States Patent
Jung et al.

(10) Patent No.: US 11,771,890 B2
(45) Date of Patent: Oct. 3, 2023

(54) BI- OR MULTIPOLAR LEAD FOR A MEDICAL DEVICE

(71) Applicants: Heraeus Deutschland GmbH & Co. KG, Hanau (DE); Heraeus Medical Components LLC, St. Paul, MN (US)

(72) Inventors: Markus Jung, Hanau (DE); Mark Hjelle, Fridley, MN (US)

(73) Assignees: Heraeus Medical Components LLC, St. Paul, MN (US); Heraeus Deutschland GmbH & Co. KG, Hanau (DE)

( * ) Notice: Subject to any disclaimer, the term of this patent is extended or adjusted under 35 U.S.C. 154(b) by 358 days.

(21) Appl. No.: 17/083,833

(22) Filed: Oct. 29, 2020

(65) Prior Publication Data
US 2022/0134091 A1    May 5, 2022

(51) Int. Cl.
*A61N 1/05*    (2006.01)
*H01B 7/02*    (2006.01)
*A61N 1/36*    (2006.01)

(52) U.S. Cl.
CPC ......... *A61N 1/0551* (2013.01); *H01B 7/0208* (2013.01); *A61N 1/3605* (2013.01)

(58) Field of Classification Search
CPC .. A61N 1/0551; A61N 1/3605; H01B 7/0208; H01B 7/048
See application file for complete search history.

(56) References Cited

U.S. PATENT DOCUMENTS

| | | | |
|---|---|---|---|
| 7,239,922 B1 * | 7/2007 | Boogaard | A61N 1/056 607/116 |
| 10,279,144 B2 | 5/2019 | Ogle et al. | |
| 2005/0027341 A1 | 2/2005 | Schrom et al. | |
| 2006/0200217 A1 | 9/2006 | Wessman | |
| 2015/0342532 A1 | 12/2015 | Basu et al. | |

* cited by examiner

*Primary Examiner* — Mark W. Bockelman
(74) *Attorney, Agent, or Firm* — Dicke, Billig & Czaja, PLLC

(57) ABSTRACT

One aspect is a bi- or multipolar lead for a medical device including: a) a cable comprising an outer insulation having at least two first openings near a distal end of the cable; an inner lumen, wherein the inner lumen is arranged coaxially to the outer insulation and extends in a longitudinal direction from a proximal end to the distal end of the cable; at least two conducting channels, wherein the at least two conducting channels are arranged between the outer insulation and the inner lumen of the cable, wherein each one of the at least two conducting channels is formed by at least one insulated conductor comprising a conductor and an insulation layer, and wherein the insulation layer of the at least one insulated conductor of each one of the at least two conducting channels comprises a second opening, which is aligned with one of the at least two first openings; b) at least two ring electrodes, wherein each one of the at least two ring electrodes surrounds the cable at a position of one of the at least two aligned first and second openings of the cable, and wherein each one of the at least two ring electrodes is selectively connected to the conductor of the at least one insulated conductor of one of the at least two conducting channels through one of the at least two aligned first and second openings.

20 Claims, 3 Drawing Sheets

BI- OR MULTIPOLAR LEAD FOR A MEDICAL DEVICE

TECHNICAL FIELD

One aspect relates to a bi- or multipolar lead, and to a process for preparing the bi- or multipolar lead. The bi- or multipolar lead is useful for a medical device, and in one embodiment for a temporary test trial lead. However, the bi- or multipolar lead may also be used in other technical fields.

BACKGROUND

Bi- or multipolar leads, and especially multipolar leads, for medical devices are usually very complex to manufacture as their preparation requires many different components which need to be assembled in many steps. Manufacturing is even more complex in case of small sized leads, which are particularly desired in the field of medical devices. The complex design of bi- or multipolar leads and the manufacturing processes for preparing the same usually lead to high prices for the end product.

The high prices of known bi- or multipolar leads are particularly problematic, if the leads are intended to be used in medical devices over a comparatively short time, e.g. in a temporary medical test trial set-up. To conduct temporary medical test trials in economically feasible manner, cheaper unipolar leads are therefore chosen for the trials. However, the use of a unipolar lead can limit the success of the test trial, which can ultimately result in less patients receiving the appropriate medical treatment in form of a permanent medical device.

Furthermore, a bi- or multipolar lead which is designed and manufactured by using a high number of single components can have a lower reliability due to more possible failure modes of the single pieces. Thus, a lower reliability can lead to a higher risk of failure for the lead, which in turn can have significant consequences, e.g. for the health of a patient when the lead is used in a medical device.

In view of the foregoing, it is desired to provide a bi- or multipolar lead which has a comparatively simple design and/or which contains comparatively little components while still having a good reliability. The bi- or multipolar lead shall be obtainable by a simple and efficient manufacturing process.

Therefore, the present embodiments are directed to the provision of an improved, or at least alternative, bi- or multipolar lead, which is useful for a medical device.

SUMMARY

One embodiment refers to a bi- or multipolar lead for a medical device. The bi- or multipolar lead for a medical device comprises
a) a cable comprising
   an outer insulation having at least two first openings near a distal end of the cable; an inner lumen,
   wherein the inner lumen is arranged coaxially to the outer insulation and extends in a longitudinal direction from a proximal end to the distal end of the cable;
   at least two conducting channels,
   wherein the at least two conducting channels are arranged between the outer insulation and the inner lumen of the cable,
   wherein each one of the at least two conducting channels is formed by at least one insulated conductor comprising a conductor and an insulation layer, and
   wherein the insulation layer of the at least one insulated conductor of each one of the at least two conducting channels comprises a second opening, which is aligned with one of the at least two first openings;
b) at least two ring electrodes,
   wherein each one of the at least two ring electrodes surrounds the cable at a position of one of at least two aligned first and second openings, and
   wherein each one of the at least two ring electrodes is selectively connected to the conductor of the at least one insulated conductor of one of the at least two conducting channels through one of the at least two aligned first and second openings.

The inventors found that by designing and manufacturing a bi- or multipolar lead according to one embodiment, a bi- or multipolar lead is available which is simple, small in size and can be prepared in an efficient way. In particular, the inventor's findings resulted in a bi- or multipolar lead having its complete lead body on the cable or coil which allows for a particularly high miniaturization. The inventive lead has comparatively little components, and especially does not need a connecting wire to attach the ring electrode to the conductor of the conducting channels. The design of the inventive lead also allows for attaching the ring electrodes at any desired position of the cable. Further to this, the inventive lead contains openings in the cable which allow for a good connectivity between the conductor of a conducting channel and the ring electrode, even for the case that no specific connecting elements are attached to the ring electrode. The second openings in the insulation of the insulated conductors are limited in size to allow for a good connectivity to the ring electrode, while at the same time maintaining the insulation towards the insulated conductor(s) of other conducting channels. Thereby, the dielectric strength/resistance against electrical short circuits towards insulated conductor(s) of other conducting channels within the lead is increased. The inventive lead can be produced in a very efficient and cheap manner so that the inventive lead may also be used for temporary applications (e.g. temporary medical test trials), where the use of other known multipolar leads would not be attractive from an economical standpoint.

Another aspect of one embodiment is a process for preparing a lead. The process comprises the steps of:
a) providing a cable comprising
   an outer insulation;
   an inner lumen,
   wherein the inner lumen is arranged coaxially to the outer insulation and extends in a longitudinal direction from a proximal end to a distal end of the cable;
   at least two conducting channels,
   wherein the at least one insulated conductor is arranged between the outer insulation and the inner lumen of the cable,
   wherein each one of the at least two conducting channels is formed by at least one insulated conductor comprising a conductor and an insulation layer;
b) providing at least two ring electrodes;
c) removing parts of the outer insulation near the distal end of the cable to create at least two first openings;
d) removing parts of the insulation layer of the at least one insulated conductor of each one of the at least two conducting channels to create at least two second openings, wherein each one of the at least two second openings is aligned with one of the at least two first openings;

e) positioning the at least two ring electrodes around the cable obtained in step d) at the position of the at least two aligned first and second openings;

f) attaching the at least two ring electrodes to the cable thereby selectively connecting each one of the at least two ring electrodes to the conductor of the at least one insulated conductor of one of the at least two conducting channels through one of the at least two aligned first and second openings.

The inventors found that the lead according to one embodiment can be prepared in an efficient and simple manner. The cable or coil on which the lead is based can be produced as a long ("endless") cable on a spool which is shortened to the desired length of the lead. The openings are introduced into the cable, which allow for directly connecting the ring electrode to the conductors of the conducting channels through a simple attachment step (e.g. by swaging).

It should be understood that for the purposes of one embodiment, the following terms have the following meanings:

A "bipolar" lead in the meaning of one embodiment is a lead comprising two conducting channels and two ring electrodes near the distal end of the cable. A "multipolar" lead is a lead comprising at least three conducting channels and at least three ring electrodes near the distal end of the cable. In general, the polarity of the lead is determined by the number of conducting channels of the lead. Since each one of the conducting channels is selectively connected to one ring electrode near the distal end of the cable, the number of conducting channels also determines the minimum number of ring electrodes near the distal end of the cable. Thus, a multipolar lead comprising four conducting channels comprises a minimum of four ring electrodes near the distal end.

"Near the distal end" of the cable means for one embodiment that a position lies within the last 30%, in one embodiment 20%, in one embodiment 10%, of the length of the cable, and "near the proximal end" means that a position lies within the first 30%, in one embodiment 20%, in one embodiment 10%, of the length of the cable.

A "first opening" in the meaning of one embodiment is a hole in the outer insulation near the distal end of the cable, by which a part of the at least one insulated conductor of one conducting channel is exposed.

A "second opening" in the meaning of one embodiment is a hole in the insulation layer of the at least one insulated conductor of one conducting channel, by which a part of the conductor of the at least one insulated conductor is exposed. The size and shape of the second opening is selected in a way that the part of the insulation layer, which is in contact with the insulation layer of an insulated conductor of another conducting channel, remains intact. In one embodiment, the second opening is located on the top side of the at least one insulated conductor. The "top side" of the at least one insulated conductor is the side of the insulated conductor, which points radially outward, as seen from the center of the cable.

An "inner lumen" in the meaning of one embodiment is a free space in the center of the bi- or multipolar lead.

A "conducting channel" in the meaning of one embodiment is a mean to selectively, electrically connect an electrical part (e.g. a ring electrode) near the proximal end of the lead with a ring electrode near the distal end of the lead.

If a second opening of the insulation layer of an insulated conductor is "aligned" with a first opening of the outer insulation, this means that the first and second openings at least partially overlap, and in one embodiment that the second opening fully overlaps with the first opening.

Where an indefinite or definite article is used when referring to a singular noun, e.g., "a", "an" or "the", this includes a plural of that noun unless anything else is specifically stated. Where the term "comprising" is used in the present description and claims, it does not exclude other elements.

For the purposes of embodiments herein, the terms "essentially consisting of" and "consisting of" are considered to be an embodiments of the term "comprising". If hereinafter a group is defined to comprise at least a certain number of embodiments, this is also to be understood to disclose a group, which in one embodiment essentially consists of only of these embodiments, or in one embodiment consists of only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" as an embodiment. Whenever the terms "including" or "having" are used, these terms are meant to be equivalent to "comprising" as defined hereinabove.

BRIEF DESCRIPTION OF THE DRAWINGS

The following schematic drawings show aspects of the invention for improving the understanding of the invention in connection with some exemplary illustrations, wherein FIGS. 1A-C show a schematic drawing of one process for preparing a multipolar lead according to one embodiment. The lead comprises six conducting channels and six ring electrodes near the distal end of the lead.

FIG. 1A exemplarily shows a cable in a radial cross section (upper) and in a longitudinal cross section (lower) for the attachment of one of the six ring electrodes. The cable comprises an outer insulation (1) having a first opening (2), which is surrounded by a circumferential recess 2A of the outer insulation. The cable further comprises an inner lumen (3) formed by an inner polymer tube (4) and six conducting channels. One conducting channel (5) is formed by two insulated conductors, wherein each one of the insulated conductors comprises a conductor (6) and an insulation layer (7). The insulation layer has a second opening (8). The second opening is positioned on the top side of the insulated conductor, and points radially outward towards the outside of the lead. The second opening is aligned with the first opening (2) in the outer insulation of the cable.

FIGS. 2A-C show a schematic drawing of another process for preparing a multipolar lead according to one embodiment. The lead comprises six conducting channels and six ring electrodes near the distal end of the lead.

FIG. 2A exemplarily shows a cable in a radial cross section (upper) and in a longitudinal cross section (lower) for the attachment of one of the six ring electrodes. The cable comprises an outer insulation (1) having a first opening (2), which is surrounded by a circumferential recess 2A. The cable further comprises an inner lumen (3) formed by an inner polymer tube (4) and six conducting channels. One conducting channel (5) is formed by two insulated conductors, wherein each one of the insulated conductors comprises a conductor (6) and an insulation layer (7). The insulation layer has a second opening (8). The second opening is positioned on the top side of the insulated conductor, and points radially outward towards the outside of the lead. The second opening is aligned with the first opening (2) in the outer insulation of the cable.

FIGS. 3A-C show a schematic drawing of yet another process for preparing a multipolar lead according to one embodiment. The lead comprises six conducting channels and six ring electrodes near the distal end of the lead.

FIG. 3A exemplarily shows a cable in a radial cross section (upper) and in a longitudinal cross section (lower) for the attachment of one of the six ring electrodes. The cable comprises a thick outer insulation (1) having a first opening (2). The cable further comprises an inner lumen (3) formed by an inner polymer tube (4) and six conducting channels. One conducting channel (5) is formed by two insulated conductors, wherein each one of the insulated conductors comprises a conductor (6) and an insulation layer (7). The insulation layer has a second opening (8). The second opening is positioned on the top side of the insulated conductor, and points radially outward towards the outside of the lead. The second opening is aligned to the first opening (2) in the outer insulation of the cable.

DETAILED DESCRIPTION

The Bi- or Multipolar Lead

One aspect of one embodiment refers to a bi- or multipolar lead for a medical device. The bi- or multipolar lead for a medical device comprises a) a cable comprising
an outer insulation having at least two first openings near a distal end of the cable;
an inner lumen,
wherein the inner lumen is arranged coaxially to the outer insulation and extends in a longitudinal direction from a proximal end to the distal end of the cable;
at least two conducting channels,
wherein the at least two conducting channels are arranged between the outer insulation and the inner lumen of the cable,
wherein each one of the at least two conducting channels is formed by at least one insulated conductor comprising a conductor and an insulation layer, and
wherein the insulation layer of the at least one insulated conductor of each one of the at least two conducting channels comprises a second opening, which is aligned with one of the at least two first openings;

b) at least two ring electrodes,
wherein each one of the at least two ring electrodes surrounds the cable at a position of one of the at least two aligned first and second openings, and
wherein each one of the at least two ring electrodes is selectively connected to the conductor of the at least one insulated conductor of one of the at least two conducting channels through one of at least two aligned first and second openings.

The bi- or multipolar lead of one embodiment comprises a cable. The cable has a proximal end and a distal end. The length the cable can be selected by the skilled person in view of the application of the inventive lead, and taking into account the present specification. For example, the cable can have a length in the range of 50 to 5000 mm, in one embodiment 100 to 2000 mm, and in one embodiment 200 to 1000 mm. In an exemplary embodiment, the cable has a length of about 500 mm.

The cable comprises an outer insulation. In one embodiment, the outer insulation has an outer diameter in the range of 200 to 5000 μm, in one embodiment 300 to 3000 μm, and in one embodiment 500 to 1500 μm. In an exemplary embodiment, the outer diameter of the outer insulation is about 700 μm. It is to be understood that the outer diameter of the outer insulation of the cable also corresponds to the outer diameter of the cable. The outer insulation has in one embodiment a wall thickness in the range of 2 to 300 μm, in one embodiment 5 to 150 μm, and in one embodiment 20 to 100 μm. According to one embodiment, the outer insulation has an outer diameter in the range of 300 to 3000 μm, and in one embodiment 500 to 1500 μm, and a wall thickness in the range of 5 to 150 μm, and in one embodiment 20 to 100 μm. In an exemplary embodiment, the wall thickness is about 60 μm.

The outer insulation in one embodiment comprises a polymer selected from the group of silicones, polyolefins (e.g. polyethylene), polyurethanes, polyimides, polyamides, polyaryletherketone (e.g. polyether ether ketone), fluorinated polymers (e.g. selected from the group of ethylene tetrafluoroethylene, polytetrafluoroethylene, perfluoroalkoxy alkanes, polyvinylidene fluorides, fluorinated ethylene propylene, and mixtures thereof), and mixtures thereof. According to one embodiment, the outer insulation comprises a polymer selected from the group of silicones, polyolefins (e.g. polyethylene), polyurethanes, polyimides, polyamides, polyaryletherketone (e.g. polyether ether ketone), fluorinated polymers (e.g. selected from the group of ethylene tetrafluoroethylene, polytetrafluoroethylene, perfluoroalkoxy alkanes, polyvinylidene fluorides, fluorinated ethylene propylene, and mixtures thereof), and mixtures thereof, and has an outer diameter in the range of 300 to 3000 µm, and in one embodiment 500 to 1500 µm, and a wall thickness in the range of 5 to 150 µm, and in one embodiment 20 to 100 µm.

The outer insulation has at least two first openings near the distal end of the cable. The at least two first openings are not particularly limited in shape as long as the opening allows for connecting a ring electrode through the opening to a material beneath the outer insulation. In one embodiment, a first opening fully covers the second opening of the insulation layer of an insulated conductor of a conducting channel.

One or more, in one embodiment each one, of the at least two first openings can be surrounded by a circumferential recess. A "circumferential recess" is a circumferential part of the cable, in which the outer insulation has a lower wall thickness compared to other parts of the outer insulation. Thus, the outer insulation of the cable is not fully removed for creating a circumferential recess in the cable. The circumferential recess may be created by laser ablation or cutting, in one embodiment laser ablation, as described below in the section "Process".

The circumferential recess can have a wall thickness of outer insulation in the range of 2 to 100 µm.

According to one embodiment, each one of the at least two first openings is surrounded by a circumferential recess. The circumferential recess can have a length and/or depth which is adjusted to the length and/or wall thickness of the ring electrodes. Thus, the circumferential recess can form a pocket into which the ring electrode can be embedded. Thereby, an isodiametric transition from the outer surface of the ring electrode to the surface of the outer insulation of the cable can be formed. Furthermore, the attached ring electrode does not pressure the remaining outer insulation of the cable of the first opening or the insulated conductors beneath the outer insulation since the dimensions of the circumferential recess can be fitted to the dimensions of the ring electrode. Of course, each one of the ring electrodes being present on the inventive lead may be, and in one embodiment are, attached to the cable in this way.

According to one embodiment, each one of the at least two first openings is surrounded by a circumferential recess of the outer insulation, wherein each one of the at least two ring electrodes is embedded into the circumferential recess of one of the at least two first openings, and each one of the ring electrodes is isodiametric to the outer diameter of the cable.

According to one embodiment, each one of the at least two first openings is surrounded by a circumferential recess of the outer insulation, wherein the depth of the circumferential recess is essentially identical to the wall thickness of one of the at least two ring electrodes. According to one embodiment, each one of the at least two first openings is surrounded by a circumferential recess of the outer insulation, wherein the length of the circumferential recess is essentially identical to the length of one of the at least two ring electrodes.

According to one embodiment, each one of the at least two first openings is surrounded by a circumferential recess of the outer insulation, wherein the depth of the circumferential recess is essentially identical to the wall thickness of one of the at least two ring electrodes, and the length of the circumferential recess is essentially identical to the length of one of the at least two ring electrodes.

According to one embodiment, each one of the at least two first openings is surrounded by a circumferential recess of the outer insulation, wherein the depth of the circumferential recess is essentially identical to the wall thickness of one of the at least two ring electrodes, and the length of the circumferential recess is essentially identical to the length of one of the at least two ring electrodes, and wherein of the each one of the at least two ring electrodes is embedded into the circumferential recess of one of the at least two first openings.

According to one embodiment, each one of the at least two first openings is surrounded by a circumferential recess of the outer insulation, wherein the depth of the circumferential recess deviates a maximum of 20%, in one embodiment 10%, and in one embodiment 5%, from the wall thickness of one of the at least two ring electrodes, and the length of the circumferential recess deviates a maximum of 20%, in one embodiment 10%, and in one embodiment 5%, from the length of one of the at least two ring electrodes, and wherein of the each one of the at least two ring electrodes is embedded into the circumferential recess of one of the at least two first openings.

According to another embodiment, each one of the at least two first openings is surrounded by a circumferential recess of the outer insulation, wherein the dimensions of the circumferential recess are adjusted to the dimensions of the ring electrodes to form pockets in the cable for the ring electrodes.

It is also possible that one or more, in one embodiment each one, of the at least two first openings is a circumferential first opening. Such a design may be preferred if the outer insulation of the cable is so thin that it is difficult or not desirable to incorporate a circumferential recess into the outer insulation. Circumferential first openings can the same advantages as described above for the circumferential recess.

According to one embodiment, at least one of the at least two first openings is a circumferential first opening of the outer insulation, wherein one of the at least two ring electrodes surrounds the cable at the position of the at least one circumferential first opening, and wherein the one ring electrode which is positioned at the least one circumferential first opening is isodiametric to the outer diameter of the cable. According to one embodiment, each one of the at least two first openings is a circumferential first opening of the outer insulation, wherein each one of the at least two ring electrodes surrounds the cable at the position of one of the at least two circumferential first openings, and wherein each one of the ring electrodes which is positioned at one of the at least two circumferential first openings is isodiametric to the outer diameter of the cable.

According to one embodiment, each one of the at least two first openings is a circumferential first opening, wherein the depth of each one of the at least two circumferential first openings is essentially identical to the wall thickness of one of the at least two ring electrodes, and the length of each one of the at least two circumferential first openings is essentially identical to the length of one of the at least two ring electrodes, and each one of the at least two ring electrodes is embedded into one of the at least two first openings.

The outer insulation of the cable has at least two first openings near the distal end of the cable, for example two to eighteen first openings. The number of the at least two first openings in the outer insulation near the distal end of the cable may be determined by the number of ring electrodes near the distal end of the cable. This is also described in further detail below in connection with the number of conducting channels and the number of ring electrodes at the distal end, which determine the polarity of the lead according to one embodiment. In one embodiment in one embodiment, the outer insulation has at least four (e.g. from four to eighteen) first openings.

The cable comprises an inner lumen, wherein the inner lumen is arranged coaxially to the outer insulation and extends in a longitudinal direction from a proximal end to the distal end of the cable. Thus, in a radial cross section of the cable, the inner lumen is located on the axis of the cable in its center.

The inner lumen has in one embodiment the dimensions that a stylet, i.e. a slender medical probe or device for implanting the lead, may be positioned and/or inserted into the lumen of the lead. In one embodiment, the inner lumen has a diameter in the range of 10 to 1000 µm, in one embodiment in the range of 50 to 500 µm, in one embodiment in the range of 200 to 400 µm. For example, the diameter of the lumen may be about 350 µm.

The inner lumen may be correspond to a hollow strand, which is only formed by the boundaries of the at least two conducting channels, which are arranged between the outer insulation and the inner lumen of the cable. Hence, in one embodiment, the inner lumen is formed by the at least two conducting channels which extend in a longitudinal direction from a proximal end to a distal end of the cable. In one embodiment, the cable does not contain an inner polymer tube which forms the inner lumen of the cable.

It is however preferred in one embodiment that the inner lumen of the cable is formed by an inner polymer tube. The inner polymer tube, may be seen as a support structure between the at least two conducting channels which are arranged between the outer insulation and the inner lumen of the cable. The inner polymer tube can provide the cable with an improved stability.

The inner polymer tube can have specific dimensions. The inner polymer tube may have an outer diameter in the range of 10 to 1000 µm, in one embodiment in the range of 50 to 500 µm, in one embodiment in the range of 200 to 400 µm. According to an exemplary embodiment, the outer diameter of the inner polymer tube is about 350 µm and the inner diameter of the inner polymer tube is about 250 µm. The inner polymer tube may have a wall thickness in the range of 2 to 200 µm, in one embodiment 10 to 100 µm, and in one embodiment 20 to 80 µm. According to one embodiment, the inner polymer tube has an outer diameter in the range of 50 to 500 µm, in one embodiment in the range of 200 to 400 µm, and a wall thickness in the range of 10 to 100 µm, and in one embodiment 20 to 80 µm.

The inner polymer tube in one embodiment comprises a polymer selected from the group of silicones, polyolefins (e.g. polyethylene), polyurethanes, polyimides, polyamides, polyaryletherketone (e.g. polyether ether ketone), fluorinated polymers (e.g. selected from the group of ethylene tetrafluorethylene, polytetrafluorethylene, perfluoroalkoxy alkanes, polyvinylidene fluorides, fluorinated ethylene propylene, and mixtures thereof), and mixtures thereof. According to one embodiment, the inner polymer tube comprises a polymer selected from the group of silicones, polyolefins (e.g. polyethylene), polyurethanes, polyimides, polyamides, polyaryletherketone (e.g. polyether ether ketone), fluorinated polymers (e.g. selected from the group of ethylene tetrafluorethylene, polytetrafluorethylene, perfluoroalkoxy alkanes, polyvinylidene fluorides, fluorinated ethylene propylene, and mixtures thereof), and mixtures thereof, and has an outer diameter in the range of 50 to 500 µm, in one embodiment in the range of 200 to 400 µm, and a wall thickness in the range of 10 to 100 µm, and in one embodiment 20 to 80 µm.

The cable comprises at least two conducting channels. For example, the cable may have between two to eighteen conducting channels. The at least two conducting channels are arranged between the outer insulation and the inner lumen of the cable. Each one of the at least two conducting channels is in electrical contact/communication with one of the at least two ring electrodes near the distal end of the cable.

In one embodiment, the cable comprises at least four conducting channels (e.g. between four and eighteen conducting channels). According to one embodiment, the cable comprises four conducting channels. According to another embodiment, the cable comprises six conducting channels.

Each one of the at least two conducting channels is formed by at least one insulated conductor. The at least one insulated conductor is in one embodiment helically wound around the inner lumen of the cable. In case the inner lumen is formed by an inner polymer tube, the at least one insulated conductor is in one embodiment helically wound around the inner polymer tube of the cable.

The at least one insulated conductor of each one of the at least two conducting channels comprises a conductor and an insulation layer.

The conductor of the at least one insulated conductor may be a single conductor or a multitude of single conductors. It is preferred in one embodiment that the conductor is a metal wire or a multitude of metal wires, which the multitude of metal wires is wound or coiled to a bundle of metal wires. The metal wire or bundle of metal wires may have a diameter in the range of 5 to 250 µm, and in one embodiment in the range of 10 to 120 µm. For example, the conductor (e.g. metal wire or bundle of metal wires) may have a diameter of about 85 µm.

The conductor of the at least one insulated conductor of the at least two conducting channels in one embodiment comprises a metal selected from the group consisting of platinum, iridium, tantalum, palladium, titanium, iron, gold, molybdenum, niob, tungsten, nickel, chromium, cobalt, stainless steel, nitinol, alloys of each one of these metals, and composite materials of each one of these metals. Suitable as a conductor is stainless steel, for example, stainless steel AISI 316L, stainless steel AISI 301 or stainless steel AISI 304. Suitable as a conductor are platinum and platinum alloys, for example, Pt/Ir 10 or Pt/Ir 20. Suitable as conductor are nickel cobalt alloys such as MP35N.

The conductor may also be coated or plated with a coating (e.g. platinum) for increasing corrosion resistance. For example, the conductor may be a Pt-plated MP35N conductor or a Pt-plated tungsten-based conductor.

The insulation layer of the at least one insulated conductor of each one of the at least two conducting channels comprises a second opening, which is aligned with one of the at least two first openings. Thereby, one first and one second opening form one aligned first and second opening. This can be understood in that the insulation layer of the at least one insulated conductor of a first conducting channel of the at least two conducting channels comprises a second opening, which is aligned with a first opening A of the outer insulation, and the insulation layer of the at least one insulated conductor of a second conducting channel of the at least two conducting channels comprises a second opening, which is aligned with a first opening B of the outer insulation. The more ring electrodes the cable or lead has, the more first and second openings there will be, and therefore the more aligned first and second openings there will be in the cable or lead. The number of aligned first and second openings is determined by the number of ring electrodes as will be understood by a skilled person.

As defined above, the size and shape of the second opening is selected in a way that the part of the insulation layer of the insulated conductor, which is in contact with the insulation layer of an insulated conductor of another conducting channel, remains intact. Thus, the remaining insulation layer of the insulated conductor, which e.g. points radially inwards to the lumen or points towards insulated conductor(s) of another conducting channel is intact and functional. Thereby, the dielectric strength/resistance against electrical short circuits is increased. This is one important finding by the inventors.

According to one embodiment, the size of the second opening(s) in the insulation layer of the insulated conductor, as seen in a cross section, does not exceed 60%, in one embodiment 50%, in one embodiment 40%, of the perimeter of the insulated conductor.

The insulation layer of the at least one conductor of the at least two conducting channels in one embodiment comprises, in one embodiment consists of, a polymer selected from the group consisting of polyolefins (e.g. polyethylene), polyurethanes, polyimides, polyamides, polyaryletherketone (e.g. polyether ether ketone), fluorinated polymers (e.g. selected from the group of ethylene tetrafluorethylene, polytetrafluoroethylene, perfluoroalkoxy alkanes, polyvinylidene fluorides, fluorinated ethylene propylene, and mixtures thereof), and mixtures thereof.

In one embodiment, the insulation layer of the at least one conductor of the at least two conducting channels has a thickness in the range of 3 to 150 µm, and in one embodiment in the range of 5 to 40 µm. For example, the insulation layer may have a thickness of about 15 µm.

Each one of the at least two conducting channels is formed by at least one insulated conductor. The number of insulated conductors which form one conducting channel can depend on how many conducting channels the cable or lead shall have, and on how stable the connection of the ring electrode to the conductor of the conducting channel shall be.

For example, one conducting channel may be formed by one insulated conductor. This can have the advantage that the cable may include a high number of conducting channels (e.g. 6, 8, 10, 12, or 18), since the single insulated conductor per conducting channels which is arranged between the outer insulation and the inner lumen occupies comparatively little space. Thus, according to one embodiment, each one of the at least two conducting channels is formed by one insulated conductor.

On the other hand, one conducting channel may be formed by two or more insulated conductors. In case one conducting channel is formed by two or more insulated conductors the second opening in the insulation layer of each one of the two or more insulated conductors is at the same position of the cable, so to allow an alignment of all second openings of the insulation layers of the two or more insulated conductors with one first opening of the outer insulation of the cable. This can have the advantage that the contact stability of one ring electrode to the conductors of one conducting channel is higher, since there is a larger contact area of conductor available for effecting the connection to the ring electrode. Thus, according to another embodiment, each one of the at least two conducting channels is formed by two or more insulated conductors (e.g. two, three, four or five insulated conductors). According to one embodiment, each one of the at least two conducting channels is formed by two or more insulated conductors, which are arranged adjacent to each other, wherein the second openings of the insulation layers of the two or more insulated conductors are at the same position in the cable, and wherein each one of the at least two ring electrodes is selectively connected to the conductors of the two or more insulated conductors of one of the at least two conducting channels.

According to one embodiment, one of the at least two conducting channels is formed by two or more insulated conductors, which are arranged adjacent to each other, wherein the second openings of the insulation layers of the two or more insulated conductors of one of the at least two conducting channels are aligned with one of the at least two first openings, and wherein the one of the at least two ring electrodes is selectively connected to the conductors of the two or more insulated conductors of one of the at least two conducting channels. According to one embodiment, each one of the at least two conducting channels is formed by two or more insulated conductors, which are arranged adjacent to each other, wherein the second openings of the insulation layers of the two or more insulated conductors of one of the at least two conducting channels are aligned with one of the at least two first openings, and wherein the each one of the at least two ring electrodes is selectively connected to the conductors of the two or more insulated conductors of one of the at least two conducting channels.

The bi- or multipolar lead of one embodiment comprises at least two ring electrodes.

Each one of the at least two ring electrodes in one embodiment comprises a metal selected from the group consisting of platinum, iridium, tantalum, palladium, titanium, iron, gold, molybdenum, niob, tungsten, nickel, chromium, cobalt, steel, nitinol, alloys of each one of these metals, and composite materials of each one of these metals. Suitable as a ring electrode is stainless steel, for example, stainless steel AISI 316L, stainless steel AISI 301 or stainless steel AISI 304. Suitable as a ring electrode is platinum and platinum alloys, for example, Pt/Ir 10 or Pt/Ir 20. Suitable as a ring electrode are nickel cobalt alloys such as MP35N.

The choice of metal for the ring electrode (and for the conductor) may depend on the use of the inventive lead. For example, if the inventive lead is to be used in a permanent medical device, the at least two ring electrodes may comprise, in one embodiment consist of, platinum or a platinum iridium alloy. If the inventive lead is to be used in a temporary medical device e.g. in a test trial, the at least two ring electrodes may comprise, in one embodiment consist of, stainless steel. However, it is to be understood that the application of the lead is not limited by the use of a specific metal.

Each one of the at least two ring electrodes may comprise a coating. Suitable coatings are metal nitrides such as TiN, metal oxides such as $IrO_2$ or conductive polymers. The surface of the at least two ring electrodes may also be surface-structured, e.g. laser-structured.

Each one of the at least two ring electrodes may have an outer diameter in the range of 200 to 5000 µm, in one embodiment in the range of 300 to 3000 µm, and in one embodiment in the range of 500 to 1500 µm. Each one of the at least two ring electrodes may have a wall thickness in the range of 10 to 200 µm, in one embodiment 10 to 100 µm, and in one embodiment 30 to 70 µm. Furthermore, each one of the at least two ring electrodes may have a length in the range of 200 to 5000 µm, in one embodiment 300 to 3000 µm, and in one embodiment in the range of 500 to 1500 µm. According to one embodiment, each one of the at least two electrodes has an outer diameter in the range of 300 to 3000 µm, and in one embodiment in the range of 500 to 1500 µm, a wall thickness in the range of 10 to 100 µm, and in one embodiment 30 to 70 µm, and a length in the range of 300 to 3000 µm, and in one embodiment in the range of 500 to 1500 µm.

According to one embodiment, each one of the at least two electrodes has an outer diameter in the range of 300 to 3000 µm, and in one embodiment in the range of 500 to 1500 µm, a wall thickness in the range of 10 to 100 µm, and in one embodiment 30 to 70 µm, and a length in the range of 300 to 3000 µm, and in one embodiment in the range of 500 to 1500 µm, and comprises a metal selected from the group consisting of platinum, iridium, tantalum, palladium, titanium, iron, gold, molybdenum, niob, tungsten, nickel, chromium, cobalt, steel, nitinol, alloys of each one of these metals, and composite materials of each one of these metals.

Each one of the at least two ring electrodes surrounds the cable at a position of one of at least two aligned first and second openings of the cable, and each one of the at least two ring electrodes is selectively connected to the conductor of the at least one insulated conductor of one of the at least two conducting channels through one of the at least two aligned first and second openings. This can be understood in that a first ring electrode of the at least two ring electrodes surrounds the cable at a position of one aligned first and second opening A and a second ring electrode of the at least two ring electrodes surrounds the cable at a position of one aligned first and second opening B, wherein the first ring electrode is selectively connected to the conductor of the at least one insulated conductor of a first conducting channel of the at least two conducting channel through the aligned first and second opening A, and the second ring electrode is selectively connected to the conductor of the at least one insulated conductor of a second conducting channel of the at least two conducting channel through the aligned first and second opening B.

As specified above, the number of conducting channels determines the minimum number of ring electrodes near the distal end of the cable. It is possible that one conducting channel is connected near the distal end of the cable to one ring electrode or to several ring electrodes (which are all on the same electrical potential). For example, it is possible that one conducting channel is connected to five ring electrodes near the distal end of the cable.

According to one embodiment, the number of the ring electrodes near the distal end of the cable and the conducting channels is the same. Thus, it is preferred in one embodiment that, when the lead has six conducting channels, there are six ring electrodes near the distal end of the cable which are selectively connected to each one of the conducting channels.

However, there may be applications of the inventive lead where it is advantageous that one or all of the conducting channels is connected to two or more ring electrodes near the distal end of the cable. In this embodiment, the number of ring electrodes near the distal end of the cable is higher than the number of conducting channels. According to one embodiment, one or each one conducting channel of the at least one conducting channel is selectively connected to two or more ring electrodes near the distal end of the cable.

There are different options how to selectively connect one ring electrode to the conductor of the at least one insulated conductor of one of the at least two conducting channels.

Figure 1A:
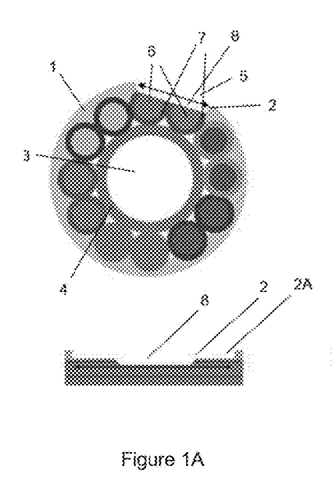
Figure 1B:
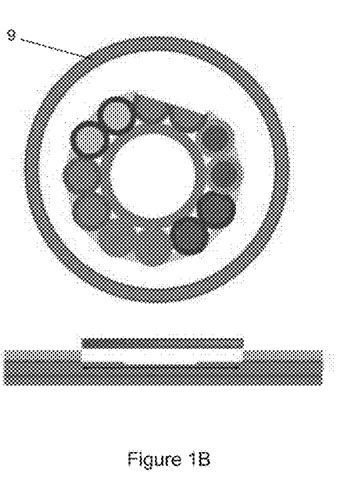
FIG. 1B shows a ring electrode (9) positioned over the aligned first and second opening (2 and 8) of one of the conducting channels of the cable in a radial cross section (upper) and a longitudinal cross section (lower). As can be seen from FIG. 1B, the ring electrode has a length and a thickness which is essentially identical to the length and the depth of the circumferential recess 2A of the outer insulation.
Figure 1C:
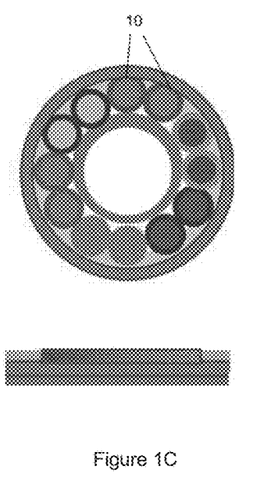
FIG. 1C shows a lead according to one embodiment, wherein the ring electrode is selectively connected (10) to the conductors of the two insulated conductors of one of the six conducting channels through one of the aligned first and second openings. The ring electrode forms an isodiametric transition with the outer insulation of the cable.

According to one embodiment, the ring electrode is directly connected to the conductor of the at least one insulated conductor of one of the at least two conducting channels. The ring electrode may have the form of a tube, which is coaxially arranged with the cable, and which is in contact with the conductor via the flat inner surface of the tube. Thus, according to one embodiment, one ring electrode, in one embodiment each one of the ring electrodes, of the at least two ring electrodes has the form of a tube and is connected to the conductor via the flat inner surface of the tube. This option is, for example, illustrated in FIG. 1C.

It is also possible that the ring electrode comprises an indentation (in one embodiment an electrode cup) which extends radially inwards from the ring electrode. In such case, the ring electrode may be directly connected to the conductor of the insulated conductor via its indentation (in one embodiment an electrode cup), which extends through one of the aligned first and second openings of the cable. An "indentation" is to be understood as a protrusion which extends radially inwards from the wall of the ring electrode. An "electrode cup" is a protrusion which extends radially inwards from the wall of the ring electrode, which is obtainable by pressing the wall of the electrode inwardly (e.g. with a pin). The indentation, in one embodiment the electrode cup, may have a width in the range of 50 to 400 µm (e.g. about 200 µm) and depth, as measured from the outer diameter of the ring electrode, in the range of 75 to 300 µm (e.g. about 130 µm).

Hence, according to one embodiment, at least one, in one embodiment each one, of the at least two ring electrodes comprises an indentation extending radially inwards from the ring electrode through one of the at least two aligned first and second openings of the cable, wherein the at least one, in one embodiment each one, of the at least two ring electrodes is connected to the conductor of the at least one insulated conductor of one of the at least two conducting channels via its indentation. This option is, for example, illustrated in FIG. 2C.

Each one of the at least two second openings can be adjusted in size and shape to the indentation of the ring electrode. It is preferred in one embodiment that each one of the at least two second openings is larger in size, in one embodiment at least 10%, than the size of the indentation of the ring electrode to provide for an optimal connectivity.

Another option is to connect the ring electrode indirectly to the conductor of the insulated conductor by using a bridge, which is positioned between the conductor and the ring electrode. Thus, according to another embodiment, at least one, in one embodiment each one, of the at least two ring electrodes is attached to a bridge comprising a metal or a conductive polymer, wherein the bridge extends radially inwards from the ring electrode through one of the at least two aligned first and second openings of the cable, and wherein the at least one of the at least two ring electrodes is connected to the conductor of the at least one insulated conductor of one of the at least two conducting channels via the bridge.

In one embodiment, the bridge comprises a metal, in one embodiment the metal is selected from the group consisting of platinum, iridium, tantalum, palladium, titanium, iron, gold, molybdenum, niob, tungsten, nickel, chromium, cobalt, steel, nitinol, alloys of each one of these metals, and composite materials of each one of these metals. The metal bridge is in one embodiment connected to the conductor by a first weld and to the ring electrode by a second weld.

In another embodiment, the bridge comprises a conductive polymer.

In case the conductor to which the ring electrode is attached is a multitude of metal wires (e.g. a coil or bundle of metal wires), the metal wires serving as contact area for the ring electrode may be welded together to improve the connection between the conductor and the ring electrode. Thus, according to one embodiment, the conductor of the at least one insulated conductor of one, in one embodiment each one, of the at least two conducting channels is a multitude of metal wires (e.g. a coil or bundle of metal wires), wherein the multitude of metal wires are welded together at the contact area for one of the at least two ring electrodes.

The lead according to one embodiment may be a bipolar lead or a multipolar lead. It is preferred in one embodiment that the lead is a multipolar lead. The multipolar lead is in one embodiment a lead with at least four conducting channels, e.g. from four to eighteen conducting channels. In such case, the lead comprises a cable comprising at least four conducting channels, e.g. from four to eighteen conducting channels.

According to one embodiment, the lead is a multipolar lead comprising:
a) a cable comprising
  an outer insulation having at least four (e.g. four to eighteen) first openings near a distal end of the cable;
  an inner lumen, wherein the inner lumen is arranged coaxially to the outer insulation and extends in a longitudinal direction from a proximal end to the distal end of the cable;
  at least four (e.g. four to eighteen) conducting channels, wherein the at least four (e.g. four to eighteen) conducting channels are arranged between the outer insulation and the inner lumen of the cable, wherein each one of the at least four conducting channels is formed by at least one insulated conductor comprising a conductor and an insulation layer, and wherein the insulation layer of the at least one insulated conductor of each one of the at least four conducting channels comprises a second opening, which is aligned with one of the at least four first openings;
b) at least four ring (e.g. four to eighteen) electrodes, wherein each one of the at least four ring electrodes surrounds the cable at a position of one of at least four aligned first and second openings, and wherein each one of the at least four ring electrodes is selectively connected to the conductor of the at least one insulated conductor of one of the at least four conducting channels through one of the at least four aligned first and second openings.

According to another embodiment, the lead is a multipolar lead comprising:
a) a cable comprising
  an outer insulation having at least six (e.g. six to eighteen) first openings near a distal end of the cable;
  an inner lumen, wherein the inner lumen is arranged coaxially to the outer insulation and extends in a longitudinal direction from a proximal end to the distal end of the cable;
  at least six (e.g. six to eighteen) conducting channels, wherein the at least six (e.g. six to eighteen) conducting channels are arranged between the outer insulation and the inner lumen of the cable, wherein each one of the at least six conducting channels is formed by at least one insulated conductor comprising a conductor and an insulation layer, and wherein the insulation layer of the at least one insulated conductor of each one of the at least six conducting channels comprises a second opening, which is aligned with one of the at least six first openings;
b) at least six ring (e.g. six to eighteen) electrodes, wherein each one of the at least six ring electrodes surrounds the cable at a position of one of at least six aligned first and second openings, and wherein each one of the at least six ring electrodes is selectively connected to the conductor of the at least one insulated conductor of one of the at least six conducting channels through one of the at least six aligned first and second openings.

According to one embodiment, the lead comprises six conducting channels.

The lead according to one embodiment comprises at least two proximal ring electrodes near the proximal end of the cable, each of which is in electrical communication with one of the at least two ring electrodes near the distal end of the cable. The number of proximal ring electrodes may be determined by the number of ring electrodes near the distal end of the cable. The at least two proximal ring electrodes are in one embodiment designed and attached to the cable the same way as the at least two distal ring electrodes. According to one embodiment, the lead comprises the same number of ring electrodes near the proximal end of the cable as it comprises ring electrodes near the distal end of the cable, wherein each one of the ring electrodes near the proximal end of the cable is in communication with one of the ring electrodes near the distal end of the cable via one conducting channel of the lead.

According to one embodiment, the outer insulation of the cable has at least two third openings near the proximal end of the cable, wherein the insulation layer of the at least one insulated conductor of each one of the at least two conducting channels comprises a fourth opening, which is aligned with one of the at least two third openings of the outer insulation, wherein the lead comprises at least two proximal ring electrodes, wherein each one of the at least two proximal ring electrodes surrounds the cable at a position of one of the at least two aligned third and fourth opening, wherein each one of the at least two proximal ring electrodes is selectively connected to the conductor of the at least one insulated conductor of one of the at least two conducting channels through one of at least two aligned third and fourth openings, and wherein each one of the at least two proximal ring electrodes is in communication with one of the at least two ring electrodes near the distal end of the cable.

According to one embodiment, the lead comprises four ring electrodes near the distal end of the cable and four ring electrodes near the proximal end of the cable, wherein each one of the four ring electrodes near the proximal end of the cable is in communication with one of the four ring electrodes near the distal end of the cable via one of four conducting channels of the lead. According to another embodiment, the lead comprises six ring electrodes near the distal end of the cable and six ring electrodes near the proximal end of the cable, wherein each one of the six ring electrodes near the proximal end of the cable is in communication with one of the six ring electrodes near the distal end of the cable via one of six conducting channels of the lead.

The at least two ring electrodes near the proximal and/or distal end of the cable may be positioned with a specific spacing to each other. The spacing of the ring electrodes can be selected and adjusted by the skilled person in view of the application of the lead, and in one embodiment in view of its medical application. According to one embodiment, the at least two ring electrodes, in one embodiment at least four ring electrodes, near the distal end of the cable are positioned with a spacing in the range of from 0.25 to 10 mm, in one embodiment in the range of from 0.5 to 6 mm, and in one embodiment in the range of from 1 to 4 mm. According to one embodiment, the at least two ring electrodes, in one embodiment at least four ring electrodes, near the proximal end of the cable are positioned with a spacing in the range of from 0.25 to 10 mm, in one embodiment in the range of from 0.5 to 6 mm, and in one embodiment in the range of from 1 to 4 mm. According to one embodiment, the at least two ring electrodes, in one embodiment at least four ring electrodes, near the proximal end of the cable are positioned with a spacing in the range of from 0.25 to 10 mm, in one embodiment in the range of from 0.5 to 6 mm, and in one embodiment in the range of from 1 to 4 mm, and the at least two ring electrodes, in one embodiment at least four ring electrodes, near the proximal end of the cable are positioned with a spacing in the range of from 0.25 to 10 mm, in one embodiment in the range of from 0.5 to 6 mm, and in one embodiment in the range of from 1 to 4 mm. The spacing between each one of the ring electrodes near one end of the cable may be the same or different, and in one embodiment is different.

The length of the lead may depend on the application of the lead, in one embodiment its medical application, and can be adjusted according to the needs of a skilled person. The lead in one embodiment has a length in the range of 50 to 5000 mm, in one embodiment 100 to 2000 mm, and in one embodiment 200 to 1000 mm. In an exemplary embodiment, the cable has a length of about 500 mm.

Furthermore, the lead may comprise one or more fixing elements at the distal end of the cable. The fixing elements of the lead may help to fix the lead for its medical application. For example, the lead may comprise barbs as fixing elements. The barbs are in one embodiment positioned on the outer surface of the outer insulation. The barbs may also be a part of the outer insulation of the cable. It is also possible that the lead comprises a spiral as a fixing element. The spiral is in one embodiment positioned at the distal end of the cable, and may have the form of a helix shaped polymer tip.

Exemplary embodiments of the lead according to one embodiment are:

A multipolar lead having a length of about 500 mm and a diameter of about 0.7 mm, which comprises:
  a) a cable comprising
    an outer insulation having six first openings near a distal end of the cable and six third openings near a proximal end of the cable;
    an inner lumen, wherein the inner lumen is arranged coaxially to the outer insulation and extends in a longitudinal direction from a proximal end to the distal end of the cable;
    six conducting channels,
    wherein the six conducting channels are arranged between the outer insulation and the inner lumen of the cable,
    wherein each one of the six conducting channels is formed by at least one insulated conductor comprising a conductor and an insulation layer, and
    wherein the insulation layer of the at least one insulated conductor of each one of the six conducting channels comprises a second opening, which is aligned with one of the six first openings and a fourth opening of the outer insulation, which is aligned with one of the six third openings of the outer insulation;
  b) six distal ring electrodes having a length of about 1.4 mm,
    wherein each one of the six distal ring electrodes surrounds the cable at a position of one of six aligned first and second openings of the cable, and
    wherein each one of the six distal ring electrodes is selectively connected to the conductor of the at least one insulated conductor of one of the six conducting channels through one of the six aligned first and second openings,
    wherein the six distal ring electrodes of a spacing of the following sequence: about 1.5 mm, about 2.5 mm, about 1.5 mm, about 2.5 mm, about 1.5 mm,
  c) six proximal ring electrodes having a length of about 1.4 mm,
    wherein each one of the six proximal ring electrodes surrounds the cable at a position of one of six aligned third and fourth openings of the cable, and
    wherein each one of the six proximal ring electrodes is selectively connected to the conductor of the at least one insulated conductor of one of the six conducting channels through one of the six aligned third and fourth openings,
    wherein the six proximal ring electrodes of a spacing of the following sequence: about 2.5 mm, about 2.5 mm, about 3.4 mm, about 2.5 mm, about 2.5 mm.

A multipolar lead having a length of about 500 mm and a diameter of about 0.7 mm, which comprises:
  a) a cable comprising
    an outer insulation having four first openings near a distal end of the cable and four third openings near a proximal end of the cable, wherein the outer insulation near the distal end comprises barbs as fixing elements;
    an inner lumen, wherein the inner lumen is arranged coaxially to the outer insulation and extends in a longitudinal direction from a proximal end to the distal end of the cable;
    four conducting channels,
    wherein the four conducting channels are arranged between the outer insulation and the inner lumen of the cable,
    wherein each one of the four conducting channels is formed by at least one insulated conductor comprising a conductor and an insulation layer, and
    wherein the insulation layer of the at least one insulated conductor of each one of the four conducting channels comprises a second opening, which is aligned with one of the four first openings and a fourth opening of the outer insulation, which is aligned with one of the four third openings of the outer insulation;
  b) four distal ring electrodes,
    wherein each one of the four distal ring electrodes surrounds the cable at a position of one of four aligned first and second openings of the cable, and
    wherein each one of the four distal ring electrodes is selectively connected to the conductor of the at least one insulated conductor of one of the four conducting channels through one of the four aligned first and second openings,
c) four proximal ring electrodes,
wherein each one of the four proximal ring electrodes surrounds the cable at a position of one of four aligned third and fourth openings of the cable, and
wherein each one of the four proximal ring electrodes is selectively connected to the conductor of the at least one insulated conductor of one of the four conducting channels through one of the four aligned third and fourth openings.

A multipolar lead having a length of about 500 mm and a diameter of about 0.7 mm, which comprises:
a) a cable comprising
an outer insulation having four first openings near a distal end of the cable and four third openings near a proximal end of the cable;
an inner lumen, wherein the inner lumen is arranged coaxially to the outer insulation and extends in a longitudinal direction from a proximal end to the distal end of the cable;
four conducting channels,
wherein the four conducting channels are arranged between the outer insulation and the inner lumen of the cable,
wherein each one of the four conducting channels is formed by at least one insulated conductor comprising a conductor and an insulation layer, and
wherein the insulation layer of the at least one insulated conductor of each one of the four conducting channels comprises a second opening, which is aligned with one of the four first openings and a fourth opening of the outer insulation, which is aligned with one of the four third openings of the outer insulation;
b) four distal ring electrodes,
wherein each one of the four distal ring electrodes surrounds the cable at a position of one of four aligned first and second openings of the cable, and
wherein each one of the four distal ring electrodes is selectively connected to the conductor of the at least one insulated conductor of one of the four conducting channels through one of the four aligned first and second openings,
c) four proximal ring electrodes,
wherein each one of the four proximal ring electrodes surrounds the cable at a position of one of four aligned third and fourth openings of the cable, and
wherein each one of the four proximal ring electrodes is selectively connected to the conductor of the at least one insulated conductor of one of the four conducting channels through one of the four aligned third and fourth openings,
d) a spiral as a fixing element at the distal end of the lead.

In each one of the exemplary embodiments defined above, it is further preferred that each one of the first openings is surrounded by a circumferential recess, which allows for embedding a ring electrode as described above.

The lead of one embodiment is useful for a medical device. The medical device may be a permanent medical device or a temporary medical device (e.g. for a medical trial). The medical device may be a pulse generator.

The lead of one embodiment is used in a medical device for neuro modulation and/or neuro stimulation. For example, the inventive lead may be used in a device for neuro modulation and/or neuro stimulation if the spinal cord, the sacral nerve, peripheral nerves, gastric stimulation, face stimulation, pelvic floor pacemaker, lung pacing, and the like.

In another aspect of one embodiment, a medical device is provided. The medical device comprises the bi- or multipolar lead according to one embodiment. The medical device may be a pulse generator. The medical device is in one embodiment used for neuro modulation and/or neuro stimulation. For example, medical device is used for neuro modulation and/or neuro stimulation if the spinal cord, the sacral nerve, peripheral nerves, gastric stimulation, face stimulation, pelvic floor pacemaker, lung pacing, and the like.

According to one embodiment, the medical device is a permanent medical device. According to another embodiment, the medical device is a temporary medical device (e.g. for a medical trial).

The Process for Preparing the Bi- or Multipolar Lead

Another aspect of one embodiment refers to the provision of a process for preparing a bi- or multipolar lead, in one embodiment a bi- or multipolar lead. The process comprises the steps of:
a) providing a cable comprising
an outer insulation;
an inner lumen,
wherein the inner lumen is arranged coaxially to the outer insulation and extends in a longitudinal direction from a proximal end to a distal end of the cable;
at least two conducting channels,
wherein the at least one insulated conductor is arranged between the outer insulation and the inner lumen of the cable,
wherein each one of the at least two conducting channels is formed by at least one insulated conductor comprising a conductor and an insulation layer;
b) providing at least two ring electrodes;
c) removing parts of the outer insulation near the distal end of the cable to create at least two first openings;
d) removing parts of the insulation layer of the at least one insulated conductor of each one of the at least two conducting channels beneath the at least two first openings to create at least two second openings,
wherein each one of the at least two second openings is aligned with one of the at least two first openings near the distal end of the cable;
e) positioning the at least two ring electrodes around the cable obtained in step d) at the position of the at least two aligned first and second openings;
attaching the at least two ring electrodes to the cable thereby selectively connecting each one of the at least two ring electrodes to the conductor of the at least one insulated conductor of one of the at least two conducting channels through one of the at least two aligned first and second openings.

It is to be understood that the process of one embodiment is a process for preparing the inventive lead as defined in detail in the foregoing section. Therefore, the embodiments and the preferred embodiments of the inventive lead as defined in the foregoing section are also disclosed in combination with the process of one embodiment. A skilled person knows in view of the present specification of the inventive lead how to adapt the process of one embodiment to arrive at a specific embodiment or preferred embodiment of the inventive lead as defined in the foregoing section. For example, if a multipolar lead is to be prepared which has four or six proximal ring electrodes and four or six distal ring electrodes as described in the foregoing section, the skilled person knows how to adapt the single steps of the inventive process for preparing such a lead. According to one embodiment, the process is a process for preparing a multipolar lead comprising at least four conducting channels as defined herein, and at least four ring electrodes as defined herein near the distal end of the cable, and in one embodiment with at least four ring electrodes as defined herein near the proximal end of the cable.

In step a) of the process a cable is provided. The cable comprises an outer insulation; an inner lumen, wherein the inner lumen is arranged coaxially to the outer insulation and extends in a longitudinal direction from a proximal end to a distal end of the cable; at least two conducting channels, wherein the at least one insulated conductor is arranged between the outer insulation and the inner lumen of the cable, wherein each one of the at least two conducting channels is formed by at least one insulated conductor comprising a conductor and an insulation layer.

Regarding the materials and the dimensions of the cable (i.e. the outer insulation, the inner lumen, the conducting channels, the conductors, the insulations layers), it is referred to the embodiments and preferred embodiments of the inventive lead as defined in the foregoing section. The same materials and dimensions of the cable are also suitable or preferred for the cable provided in step a).

The cable provided in step a) is in one embodiment manufactured by preparing the conducting channels from at least one metal wire which is coated by an insulation layer. The conducting channels may be bundled or stranded. The conducting channels are wrapped around the inner lumen or the inner polymer tube forming the lumen. Then, the conducting channels may be coated with an outer insulation e.g. by polymer extrusion or by drawing a polymer tube over the conducting channels. This way an "endless" cable can be produced on a spool, which is inexpensive, and easily processed.

Hence, according to one embodiment, the cable is provided in step a) by a process comprising the steps of: insulating a metal wire or a multitude of metal wires with an insulation layer to obtain at least one insulated conductor for each one of the at least two conducting channels; winding, in one embodiment in a helically way, the at least one insulated conductor of each one of the at least two conducting channels obtained in the previous step around an inner lumen (e.g. a hollow space or an inner polymer tube); providing the at least one insulated conductor of each one of the at least two conducting channels obtained in the previous step with an outer insulation.

The processes for providing the cable of step a) are known to the skilled person, and can be selected according to the desired embodiment of the cable.

Exemplary embodiments of the cable provided in step a) are:

A cable having a diameter of about 0.7 mm, which comprises an
  outer insulation, wherein the wall thickness of the outer insulation is about 60 µm;
  an inner lumen, wherein the inner lumen is arranged coaxially to the outer insulation and extends in a longitudinal direction from a proximal end to the distal end of the cable, wherein the inner lumen is formed by an inner polymer tube having an outer diameter of about 350 µm and an inner diameter of about 250 µm;
  six conducting channels, wherein the six conducting channels are arranged between the outer insulation and the inner polymer tube of the cable, wherein each one of the six conducting channels is formed by two insulated conductors comprising a conductor and an insulation layer, wherein the conductor has a diameter of about 85 µm insulation layer has a thickness of about 15 µm.

A cable having a diameter of about 0.77 mm, which comprises an
  outer insulation, wherein the wall thickness of the outer insulation is about 80 µm;
  an inner lumen, wherein the inner lumen is arranged coaxially to the outer insulation and extends in a longitudinal direction from a proximal end to the distal end of the cable, wherein the inner lumen has a diameter of about 350 µm, and wherein the inner lumen does not contain an inner polymer tube;
  six conducting channels, wherein the six conducting channels are arranged between the outer insulation and the inner polymer tube of the cable, wherein each one of the six conducting channels is formed by two insulated conductors comprising a conductor and an insulation layer, wherein the conductor has a diameter of about 90 µm insulation layer has a thickness of about 20 µm.

In step b) of the process, at least two ring electrodes are provided.

Regarding the material and the at least two ring electrodes (e.g. the metal, the coating, etc), it is referred to the embodiments and preferred embodiments of the inventive lead as defined in the foregoing section. The same materials of the at least two ring electrodes are also suitable or preferred for the at least two ring electrodes provided in step b).

The dimensions of the at least two ring electrodes provided in step b) are comparable to those of the at least two ring electrodes attached near the distal end of the cable of the inventive lead. However, it is to be understood that the diameter of the at least two ring electrodes provided in step b) of the process has to be larger than the desired final diameter of the ring electrodes on the inventive lead, to make up for the reduction of the ring electrodes diameter during the attaching step f). For example, of the desired final diameter of a ring electrode on the lead is 0.7 mm, then a ring electrode having a diameter of 0.83 mm may be provided in step b) of the process.

Each one of the at least two ring electrodes provided in step b) may have an outer diameter in the range of 200 to 5500 µm, in one embodiment in the range of 300 to 3300 µm, and in one embodiment in the range of 500 to 1750 µm. Each one of the at least two ring electrodes may have a wall thickness in the range of 10 to 200 µm, in one embodiment 10 to 150 µm, and in one embodiment 30 to 100 µm. Furthermore, each one of the at least two ring electrodes may have a length in the range of 200 to 5000 µm, in one embodiment 300 to 3000 µm, and in one embodiment in the range of 500 to 1500 µm. According to one embodiment, each one of the at least two electrodes has an outer diameter in the range of 300 to 3300 µm, and in one embodiment in the range of 500 to 1750 µm, a wall thickness in the range of 10 to 150 µm, and in one embodiment 30 to 100 µm, and a length in the range of 300 to 3000 µm, and in one embodiment in the range of 500 to 1500 µm.

The at least two ring electrodes provided in step b) may comprise an indentation (in one embodiment an electrode cup) which extends radially inwards from the ring electrode. In one embodiment, the indentation is an electrode cup, which is obtained by pressing in the wall of the ring electrode with a pin. The indentation, in one embodiment the electrode cup, may have a width in the range of 50 to 400

μm (e.g. about 200 μm) and depth, as measured from the outer diameter of the ring electrode, in the range of 75 to 300 μm (e.g. about 130 μm).

Depending on the exact geometry of the at least two ring electrodes (e.g. with or without indentation), the at least two ring electrodes may be provided in step b) in different ways.

According to one embodiment, each one of the at least two ring electrodes are provided in step b) by a deep drawing process comprising the steps of:
- forming a metal strip into a metal ring having a desired final geometry of the ring electrode by using a press and a deep-drawing die,
- further processing the metal ring by one or more steps selected from surface structuring, cutting, deburring, and polishing (e.g. magnetic vibratory grinding).

According to another embodiment, each one the at least two ring electrodes is provided in step b) by a tube forming process comprising the steps of:
- providing a metal tube having a desired wall thickness and an outer diameter of the ring electrode,
- forming an indentation in the wall of the metal tube, which extends radially inwards from the metal tube, in one embodiment by pressing in the wall of the ring electrode with a pin,
- further processing the intended metal tube by one or more steps selected from the group of surface structuring, cutting, deburring, and polishing (e.g. magnetic vibratory grinding).

The processes for providing the at least two ring electrodes of step b) are known to the skilled person, and can be selected according to the desired at least two ring electrodes of the inventive lead.

An exemplary embodiment of each one of the at least two ring electrodes provided in step b) is:

A ring electrode having of a length of about 1400 μm, an inner diameter of about 750 μm, and an outer diameter of about 830 μm, and comprising an electrode cup having a width of about 200 μm and a depth, as measured from the outer diameter of the ring electrode, of about 130 μm.

Figure 2A:
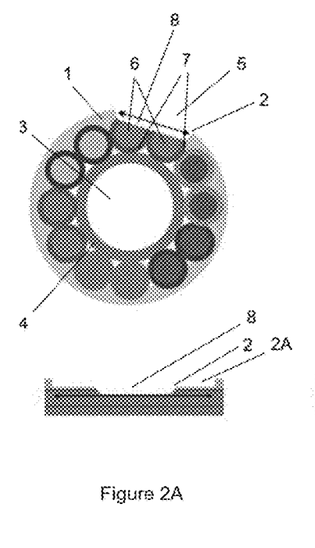
Figure 2B:
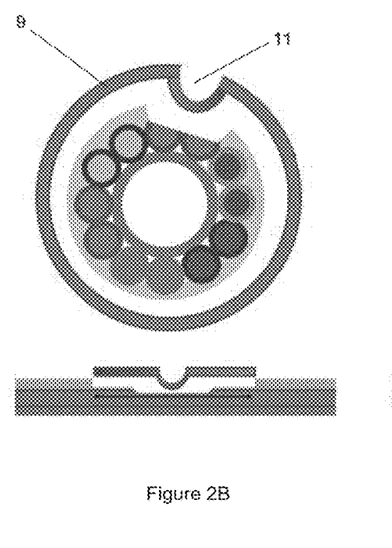
FIG. 2B shows a ring electrode (9) positioned over the aligned first and second opening (2 and 8) of the cable in a radial cross section (upper) and a longitudinal cross section (lower). The ring electrode comprises an electrode cup (11), which extends radially inwards in the direction of the cable. As can be seen from FIG. 2B, the ring electrode has a length and a thickness which is essentially identical to the length and the depth of the circumferential recess 2A of the outer insulation.
Figure 2C:
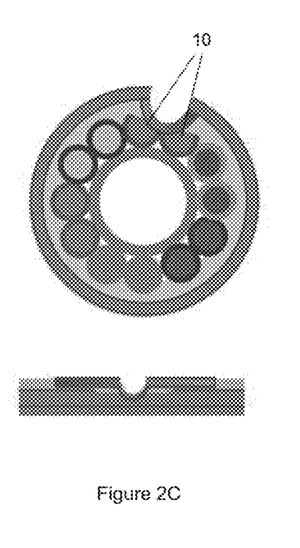
FIG. 2C shows a lead according to one embodiment, wherein the ring electrode is selectively connected (10) via the electrode cup to the conductors of the two insulated conductors of one of the six conducting channels through one of the aligned first and second openings. The ring electrode forms an isodiametric transition with the outer insulation of the cable.
Figure 3A:
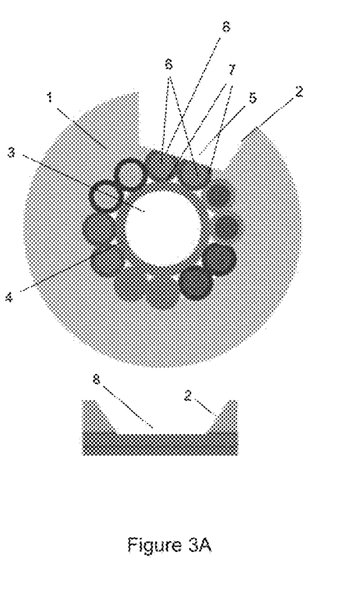
Figure 3B:
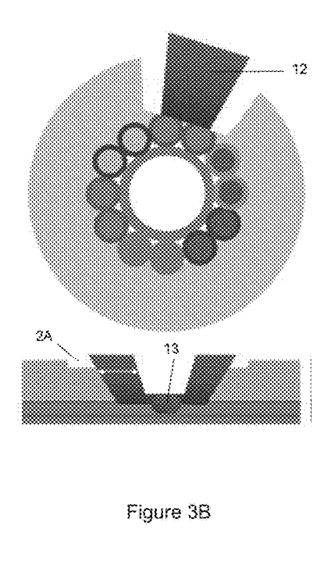
FIG. 3B shows a cable comprising a metal bridge (12) in a radial cross section (upper) and a longitudinal cross section (lower). The metal bridge is attached to the conductors of the two insulated conductors of one of the six conducting channels by a first weld (13). It can further be seen in FIG. 3B that the first opening is surrounded by a circumferential recess 2A of the outer insulation.
Figure 3C:
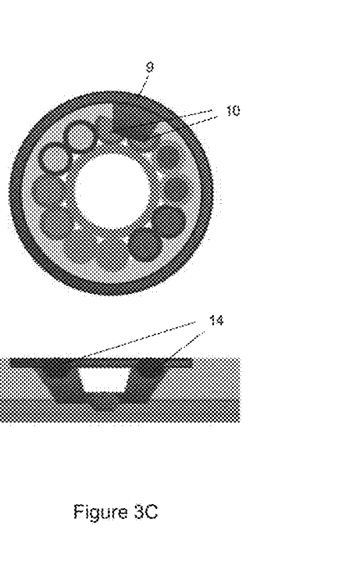
FIG. 3C shows a lead according to one embodiment, wherein the ring electrode (9) is welded to the metal bridge by a second weld (14), thereby selectively connecting (10) the ring electrode to the conductors of the two insulated conductors of one of the six conducting channels through one of the aligned first and second openings. The ring electrode has essentially the same length and wall thickness as the length and depth of the circumferential recess of the outer insulation. The ring electrode forms an isodiametric transition with the outer insulation of the cable.

In step c) and d) of the process, parts of the outer insulation near the distal end of the cable are removed to create at least two first openings, and parts of the insulation layer of the at least one insulated conductor of each one of the at least two conducting channels beneath the at least two first openings are removed to create at least two second openings, wherein each one of the at least two second openings is aligned with one of the at least two first openings. In view of the definition of the term "second opening" above, it is to be understood that the part of the insulation layer of the at least one insulated conductor of each one of the at least two conducting channels which is removed in step d) is a part of the insulation layer which is not in contact with an insulation layer of an insulated conductor of another conducting channel. This is also illustrated in FIG. 1A to 3A. In one embodiment, the part of the insulation layer which is removed in step c) is a part on the top side of the insulated conductor.

Steps c) and d) can be carried out separately or together, and are in one embodiment carried out together.

Step c) and/or step d) is in one embodiment carried out by laser ablation or by cutting. According to one embodiment, the steps c) and d) are carried out by laser ablation or by cutting, and in one embodiment by laser ablation.

In step c) of the process, parts of the outer insulation at the contact points are in one embodiment removed by laser ablation or mechanical cutting without damaging the insulation layer underneath the insulated conductor and the insulation layer of an insulated conductor of a neighboring conducting channel. The area of the outer insulation, which is removed in step c) at one contact point, may be larger than the area of the insulation layer removed in step d) at the same contact point. This can simplify taking out parts of the conductor of the insulated conductor in a subsequent step d2).

According to one embodiment, step c) further comprises removing circumferential parts of the outer insulation to create a circumferential recess, which surrounds one of each one of the at least two first openings. The advantage of the circumferential recess is described in the foregoing section. In brief, a circumferential recess allows for attaching a ring electrode in an isodiametric way, which is a particularly desirable design, and ensures that the outer insulation around the first opening is not squeezed by the attached ring electrode.

According to one embodiment, step c) further comprises removing circumferential parts of the outer insulation to create a circumferential recess, which surrounds one of each one of the at least two first openings, and wherein the ring electrodes are embedded in step f) into the circumferential recesses of the cable in a way to form an isodiametric transition between the surface of the cable and the surface of the at least two ring electrodes.

According to one embodiment, step c) further comprises removing circumferential parts of the outer insulation to create a circumferential recess, which surrounds one of each one of the at least two first openings, wherein the depth of the circumferential recess deviates a maximum of 20%, in one embodiment 10%, in one embodiment 5%, from the wall thickness of the ring electrodes provided in step b), and wherein the length of the circumferential recess deviates a maximum of 20%, in one embodiment 10%, in one embodiment 5%, from the length of the ring electrodes provided in step b).

According to one embodiment, step c) further comprises removing circumferential parts of the outer insulation to create a circumferential recess, which surrounds one of each one of the at least two first openings, wherein the depth of the circumferential recess is essentially identical to the wall thickness of the two ring electrodes provided in step b), and wherein the length of the circumferential recess is essentially identical to the length of the ring electrodes provided in step b).

According to another embodiment, circumferential parts of the outer insulation are removed in step c) to create at least two circumferential first openings. According to one embodiment, circumferential parts of the outer insulation are removed in step c) to create at least two circumferential first openings, and wherein the at least two ring electrodes are attached in step f) to the cable in a way to form an isodiametric transition between the surface of the cable and the surface of the at least two ring electrodes. According to one embodiment, circumferential parts of the outer insulation are removed in step c) to create at least two circumferential first openings, and wherein step f) further comprises embedding each one of the at least two ring electrodes into one of the at least two circumferential first openings.

In step d) of the process, parts of the insulation layer of the at least one insulated conductor at the contact points are in one embodiment removed by laser ablation or mechanical cutting without damaging the insulation layer underneath the insulated conductor and the insulation layer of an insulated conductor of a neighboring conducting channel. The insulation layer of the at least one insulated conductor is in one embodiment removed in step d) only to an extent which allows for taking out the conductor of the insulated conductor in a subsequent step d2).

Step d) in one embodiment comprises a step d2) of taking out parts of the conductor of the at least one insulated conductor of each one of the at least two conducting channels of the cable. A part of the conductor may be taken out the second opening of the insulation layer to allow for a better connecting with the ring electrode in step f). If necessary, the conductor may be cut to ease the taking out of parts of the conductor.

Furthermore, if the conductor of the at least one insulated conductor of one, in one embodiment each one, of the at least two conducting channels comprises a multitude of metal wires (e.g. a coil or bundle of metal wires), the multitude of metal wires which are exposed in the second opening obtained in step d) may be welded together to improve contact stability and/or the connecting process in subsequent step f). Thus, according to one embodiment, the conductor of the at least one insulated conductor of one, in one embodiment each one, of the at least two conducting channels of the cable provided in step a) comprises a multitude of metal wires (e.g. a bundle of metal wires), and step d) comprises a step d3) of welding together the multitude of metal wires in the second opening.

According to one embodiment, step c) further comprises removing circumferential parts of the outer insulation to create a circumferential recess, which surrounds the first opening of each one of the at least two first openings, and the insulation layer of the at least one insulated conductor is removed in step d) on the top side of the insulated conductor, and parts of the conductor of the at least one insulated conductor of each one of the at least two conducting channels of the cable are taken out in a step d2), optionally step d2) comprises the cutting of the conductor of the at least one insulated conductor of each one of the at least two conducting channels of the cable before taking out.

As described in the foregoing section, it is possible to attach each one of the at least two ring electrodes to the conductor of the at least one insulated conductor of one of the at least two conducting channels via a bridge comprising a metal or a conductive polymer.

According to one embodiment, step d) comprises a step of connecting a bridge comprising a metal or a conductive polymer to the conductor of the at least one insulated conductor of one, in one embodiment each one, of the at least two conducting channels in one, in one embodiment each one, of the at least two aligned first and second openings, and wherein in step f) one, in one embodiment each one, of the at least two ring electrodes is selectively connected to the conductor of the at least one insulated conductor of one of the at least two conducting channels via the bridge. In case, step d) comprises the step d2) and/or step d3) as defined above, the bridge is connected to the conductor after step d2) and/or step d3).

If the bridge comprises a metal, the bridge is in one embodiment attached to the conductor by a first weld, and to the ring electrode by a second weld.

In step e) of the process, the at least two ring electrodes are positioned around the cable obtained in step d) at the position of the at least two aligned first and second openings. The positioning of the ring electrodes may be done by any suitable means known to the skilled person.

In step f) of the process, the at least two ring electrodes are attached to the cable thereby selectively connecting each one of the at least two ring electrodes to the conductor of the at least one insulated conductor of one of the at least two conducting channels through one of the at least two aligned first and second openings.

According to one embodiment, the at least two ring electrodes are attached in step e) by swaging. It is one advantage of one embodiment that step f) may be carried out by swaging without the use of a welding step. This simplifies the inventive process compares to known processes. Thus, according to one embodiment, step f) does not contain a welding of the at least two ring electrodes. It is however possible to attach the at least two ring electrodes to the conductor by welding. Thus, according to another embodiment, the at least two ring electrodes are attached in step f) by welding. According to another embodiment, the at least two ring electrodes are attached in step e) by swaging and welding.

The process according to one embodiment may comprise additional process steps of capping one end of the lead, adding fixing elements to the distal end of the lead (e.g. a spiral), cutting the outer insulation of the lead to form fixing elements (e.g. barbs), surface structuring (e.g. stamping) the at least two ring electrodes, finishing the lead, and the like. Such processes are known to the skilled person and can be selected and adjusted according to the desired application of the lead, in one embodiment to the desired application in a medical device.

The features disclosed in the claims, the specification, and the drawings maybe essential for different embodiments of the claimed invention, both separately and in any combination with each other.

The invention claimed is:
1. A bi- or multipolar lead for a medical device comprising:
   a) a cable comprising
      an outer insulation having at least two first openings near a distal end of the cable;
      an inner lumen,
      wherein the inner lumen is arranged coaxially to the outer insulation and extends in a longitudinal direction from a proximal end to the distal end of the cable;
      at least two conducting channels,
      wherein the at least two conducting channels are arranged between the outer insulation and the inner lumen of the cable,
      wherein each one of the at least two conducting channels is formed by at least one insulated conductor comprising a conductor and an insulation layer, and
      wherein the insulation layer of the at least one insulated conductor of each one of the at least two conducting channels comprises a second opening, which is aligned with one of the at least two first openings; and
   b) at least two ring electrodes,
      wherein each one of the at least two ring electrodes surrounds the cable at a position of one of at least two aligned first and second openings of the cable, and
      wherein each one of the at least two ring electrodes is directly and selectively connected to the conductor of the at least one insulated conductor of one of the at least two conducting channels through one of the at least two aligned first and second openings.

2. The lead according to claim 1, wherein the lead is a multipolar lead comprising:
   a) a cable comprising
      an outer insulation having at least four first openings near a distal end of the cable;
      an inner lumen,
      wherein the inner lumen is arranged coaxially to the outer insulation and extends in a longitudinal direction from a proximal end to the distal end of the cable;
      at least four conducting channels,
      wherein the at least four conducting channels are arranged between the outer insulation and the inner lumen of the cable,
      wherein each one of the at least four conducting channels is formed by at least one insulated conductor comprising a conductor and an insulation layer, and
      wherein the insulation layer of the at least one insulated conductor of each one of the at least four conducting channels comprises a second opening, which is aligned with one of the at least four first openings;
   b) at least four ring electrodes,
      wherein each one of the at least four ring electrodes surrounds the cable at a position of one of at least four aligned first and second openings of the cable, and
      wherein each one of the at least four ring electrodes is directly and selectively connected to the conductor of the at least one insulated conductor of one of the at least four conducting channels through one of the at least four aligned first and second openings.

3. The lead according to claim 1,
   wherein each one of the at least two conducting channels is formed by two or more insulated conductors, which are arranged adjacent to each other,
   wherein the second openings of the insulation layers of the two or more insulated conductors of one of the at least two conducting channels are aligned with one of the at least two first openings, and
   wherein each one of the at least two ring electrodes is selectively connected to the conductors of the two or more insulated conductors of one of the at least two conducting channels.

4. The lead according to claim 1,
   wherein the lead comprises the same number of ring electrodes near the proximal end of the cable as it comprises ring electrodes near the distal end of the cable,
   wherein each one of the ring electrodes near the proximal end of the cable is in communication with one of the ring electrodes near the distal end of the cable via one conducting channel of the lead.

5. The lead according to claim 1, wherein the outer insulation of the cable has one or more of:
   an outer diameter in the range of 200 to 5000 μm, and
   a wall thickness in the range of 2 to 300 μm, and
   wherein the at least two ring electrodes have one or more of:
   an outer diameter in the range of 200 to 5000 μm,
   an wall thickness in the range of 10 to 200 μm, and
   a length in the range of 200 to 5000 μm.

6. The lead according to claim 1, wherein the inner lumen has a diameter in the range of 10 to 1000 μm and is formed by an inner polymer tube.

7. The lead according to claim 1,
   wherein the conductor of the at least one insulated conductor of the at least two conducting channels comprises a metal selected from the group consisting of platinum, iridium, tantalum, palladium, titanium, iron, gold, molybdenum, niob, tungsten, nickel, chromium, cobalt, steel, nitinol, alloys of each one of these metals, and composite materials of each one of these metals; and
   wherein the at least two ring electrodes comprise a metal selected from the group consisting of platinum, iridium, tantalum, palladium, titanium, iron, gold, molybdenum, niob, tungsten, nickel, chromium, cobalt, steel, nitinol, alloys of each one of these metals, and composite materials of each one of these metals.

8. The lead according to claim 1,
   wherein each one of the at least two ring electrodes comprises an indentation extending radially inwards from the ring electrode through one of the at least two aligned first and second openings of the cable, and
   wherein each one of the at least two ring electrodes is connected to the conductor of the at least one insulated conductor of one of the at least two conducting channels via its indentation.

9. The lead according to claim 1,
   wherein each one of the at least two first openings is a circumferential first opening of the outer insulation,
   wherein each one of the at least two ring electrodes surrounds the cable at the position of one of the at least two circumferential first openings, and
   wherein each one of the ring electrodes which is positioned at one of the at least two circumferential first openings is isodiametric to the outer diameter of the cable.

10. The lead according to claim 1,
    wherein each one of the at least two first openings is surrounded by a circumferential recess of the outer insulation,
    wherein each one of the at least two ring electrodes is embedded into the circumferential recess of one of the at least two first openings, and
    wherein each one of the ring electrodes is isodiametric to the outer diameter of the cable.

11. The lead according to claim 1,
    wherein each one of the at least two first openings is surrounded by a circumferential recess of the outer insulation,
    wherein the depth of the circumferential recess is essentially identical to the wall thickness of one of the at least two ring electrodes, and the length of the circumferential recess is essentially identical to the length of one of the at least two ring electrodes, and
    wherein each one of the at least two ring electrodes is embedded into the circumferential recess of one of the at least two first openings.

12. The lead according to claim 1, wherein each one of the at least two ring electrodes have the form of a tube and are connected to the conductor via the flat inner surface of the tube.

13. A bi- or multipolar lead for a medical device comprising:
   a) a cable comprising
      an outer insulation having at least two first openings near a distal end of the cable;
      an inner lumen,
      wherein the inner lumen is arranged coaxially to the outer insulation and extends in a longitudinal direction from a proximal end to the distal end of the cable;
      at least two conducting channels,
      wherein the at least two conducting channels are arranged between the outer insulation and the inner lumen of the cable,
      wherein each one of the at least two conducting channels is formed by at least one insulated conductor comprising a conductor and an insulation layer, and
      wherein the insulation layer of the at least one insulated conductor of each one of the at least two conducting channels comprises a second opening, which is aligned with one of the at least two first openings; and
   b) at least two ring electrodes,
      wherein each one of the at least two ring electrodes surrounds the cable at a position of one of at least two aligned first and second openings of the cable,
      wherein each one of the at least two ring electrodes is selectively connected to the conductor of the at least one insulated conductor of one of the at least two conducting channels through one of the at least two aligned first and second openings
      wherein each one of the at least two ring electrodes is attached to a bridge comprising a metal or a conductive polymer, wherein the bridge extends radially inwards from the ring electrode through one of the at least two aligned first and second openings of the cable, and wherein each one of the at least two ring electrodes is connected to the conductor of the at least one insulated conductor of one of the at least two conducting channels via the bridge.

14. The lead according to claim 13, wherein the lead is a multipolar lead comprising:
   a) a cable comprising
      an outer insulation having at least four first openings near a distal end of the cable;
      an inner lumen,
      wherein the inner lumen is arranged coaxially to the outer insulation and extends in a longitudinal direction from a proximal end to the distal end of the cable;
      at least four conducting channels,
      wherein the at least four conducting channels are arranged between the outer insulation and the inner lumen of the cable,
      wherein each one of the at least four conducting channels is formed by at least one insulated conductor comprising a conductor and an insulation layer, and
      wherein the insulation layer of the at least one insulated conductor of each one of the at least four conducting channels comprises a second opening, which is aligned with one of the at least four first openings;
   b) at least four ring electrodes,
      wherein each one of the at least four ring electrodes surrounds the cable at a position of one of at least four aligned first and second openings of the cable,
      wherein each one of the at least four ring electrodes is attached to a bridge comprising a metal or a conductive polymer, wherein the bridge extends radially inwards from the ring electrode through one of the at least two aligned first and second openings of the cable, and
      wherein each one of the at least four ring electrodes is selectively connected to the conductor of the at least one insulated conductor of one of the at least four conducting channels through one of the at least two aligned first and second openings via the bridge.

15. The lead according to claim 13,
   wherein each one of the at least two conducting channels is formed by two or more insulated conductors, which are arranged adjacent to each other,
   wherein the second openings of the insulation layers of the two or more insulated conductors of one of the at least two conducting channels are aligned with one of the at least two first openings, and
   wherein each one of the at least two ring electrodes is selectively connected to the conductors of the two or more insulated conductors of one of the at least two conducting channels.

16. The lead according to claim 13,
   wherein the lead comprises the same number of ring electrodes near the proximal end of the cable as it comprises ring electrodes near the distal end of the cable, and
   wherein each one of the ring electrodes near the proximal end of the cable is in communication with one of the ring electrodes near the distal end of the cable via one conducting channel of the lead.

17. The lead according to claim 13, wherein the outer insulation of the cable has one or more of:
   an outer diameter in the range of 200 to 5000 µm, and
   a wall thickness in the range of 2 to 300 µm, and
   wherein the at least two ring electrodes have one or more of:
      an outer diameter in the range of 200 to 5000 µm,
      an wall thickness in the range of 10 to 200 µm, and
      a length in the range of 200 to 5000 µm.

18. The lead according to claim 13, wherein the inner lumen has a diameter in the range of 10 to 1000 µm, and optionally is formed by an inner polymer tube.

19. The lead according to claim 13,
   wherein the conductor of the at least one insulated conductor of the at least two conducting channels comprises a metal selected from the group consisting of platinum, iridium, tantalum, palladium, titanium, iron, gold, molybdenum, niob, tungsten, nickel, chromium, cobalt, steel, nitinol, alloys of each one of these metals, and composite materials of each one of these metals, and
   wherein the at least two ring electrodes comprise a metal selected from the group consisting of platinum, iridium, tantalum, palladium, titanium, iron, gold, molybdenum, niob, tungsten, nickel, chromium, cobalt, steel, nitinol, alloys of each one of these metals, and composite materials of each one of these metals.

20. The lead according to claim 13, the lead being further defined by one of the following characteristics (i) to (iii):
   (i) wherein each one of the at least two first openings is a circumferential first opening of the outer insulation,
      wherein each one of the at least two ring electrodes surrounds the cable at the position of one of the at least two circumferential first openings, and wherein each one of the ring electrodes which is positioned at one of the at least two circumferential first openings is isodiametric to the outer diameter of the cable, (ii) wherein each one of the at least two first openings is surrounded by a circumferential recess of the outer insulation, wherein each one of the at least two ring electrodes is embedded into the circumferential recess of one of the at least two first openings, and wherein each one of the ring electrodes is isodiametric to the outer diameter of the cable, and (iii) wherein each one of the at least two first openings is surrounded by a circumferential recess of the outer insulation, wherein the depth of the circumferential recess is essentially identical to the wall thickness of one of the at least two ring electrodes, and the length of the circumferential recess is essentially identical to the length of one of the at least two ring electrodes, and wherein each one of the at least two ring electrodes is embedded into the circumferential recess of one of the at least two first openings.

\* \* \* \* \*